(12) United States Patent
Johansen et al.

(10) Patent No.: US 7,141,548 B2
(45) Date of Patent: Nov. 28, 2006

(54) PREVENTION OF HYPERINSULINEMIA IN SUBJECTS UNDERGOING GROWTH HORMONE (GH) TREATMENT

(75) Inventors: Thue Johansen, Copenahgen O (DK); Kjell Malmlof, Kalmar (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/861,004

(22) Filed: Jun. 4, 2004

(65) Prior Publication Data

US 2004/0220109 A1 Nov. 4, 2004

Related U.S. Application Data

(63) Continuation of application No. 10/822,020, filed on Apr. 9, 2004, now abandoned.

(60) Provisional application No. 60/467,079, filed on May 1, 2003.

(30) Foreign Application Priority Data

Apr. 9, 2003 (DK) ............................... 2003 00548

(51) Int. Cl.
*A61K 38/00* (2006.01)
*A61K 39/00* (2006.01)

(52) U.S. Cl. ...................... 514/12; 424/198.1; 530/399
(58) Field of Classification Search ................. 514/12, 514/866, 909; 436/71; 424/9.1
See application file for complete search history.

(56) References Cited

OTHER PUBLICATIONS

Cefalu, W. Exp. Biol. and Med. 226: 13-26, 2001.*
Consensus Development Conference on Insulin Resistaance, Diabetes Care vol. 21, 310-314, 1998.*
Nam et al., Int. J. of Obesity, 25: 1101-1107, 2001.*
International Search Report Jun. 19, 2003.
Malmöff, K. et al., Eur J. Endo, vol. 146, pp. 121-128 (2002).
Malmöff, K. et al., Horm Metab Res, vol. 35, pp. 236-242 (2003).
Johansen, T. et al., Horm Metab Res, vol. 35, pp. 243-250 (2003).
Rizza, RA. et al., Diabetes, vol. 31, pp. 663-669 (1982) (Abstract).
Skaggs, SR. et al., Horm Res, vol. 35, pp. 19-24 (1991) (Abstract).
Snyder DK. et al., J Clin Endocrinol Metab., vol. 69, pp. 745-752 (1989) (Abstract).
Richelsen B. et al., Am J Physiol., vol. 266, pp. E211-E216 (1994).
Clemmons DR. et al., J Clin Endocrinal Metab, vol. 64, pp. 878-883 (1987.
Kim KR. et al., Horm Res, vol. 51, pp. 78-84 (1999).
Norrelund H. et al., Clin Endocrinol, vol. 52, pp. 305-312 (2000).
Lauterio TJ. et al., Metab Clin Exp, vol. 46, pp. 210-216 (1997).
Rasmussen MH. et al., J Clin Endocrinol Metab, vol. 80, pp. 1407-1415 (1995).
Johannsson et al., Journal of Clinical Endocrinology and Metabolism, vol. 83(3), pp. 727-734 (1997).
Segerlantz et. al., J Clin Endocrinol Metab, vol. 86, No. 12, pp. 5813-5818 (2001).
Nielsen et. al., Diabetes, vol. 50, pp. 2301-2308 (2001).
Piatti, et. al., J Clin Endocrinol Metab, vol. 84, No. 5, pp. 1658-1663 (1999).
Nam, et. al., Int J Obes, vol. 25, pp. 1101-1107 (2001).
Malmlöf, et. al., Horm Metab Res, vol. 35, pp. 236-242 (2003).
Sturiale, et. al., Horm Res, vol. 48, supplement, p. 190 (1997).
Metcalfe, et. al., Diabetologia, vol. 20, pp. 123-128 (1981).
Nielsen, S. Growth Horm IGF Res, vol. 12, pp. 425-433 (2002).

* cited by examiner

*Primary Examiner*—Eileen B. O'Hara
*Assistant Examiner*—Gyan Chandra
(74) *Attorney, Agent, or Firm*—Len S. Smith; Reza Green; Richard Bork

(57) ABSTRACT

The present invention provides methods and compositions for preventing hyperinsulinemia that can result from therapeutic administration of growth hormone. The methods are carried out by imposing a restricted high-fat diet and/or by administering one or more drugs that lower serum lipids.

6 Claims, 4 Drawing Sheets

2

Figure 1:
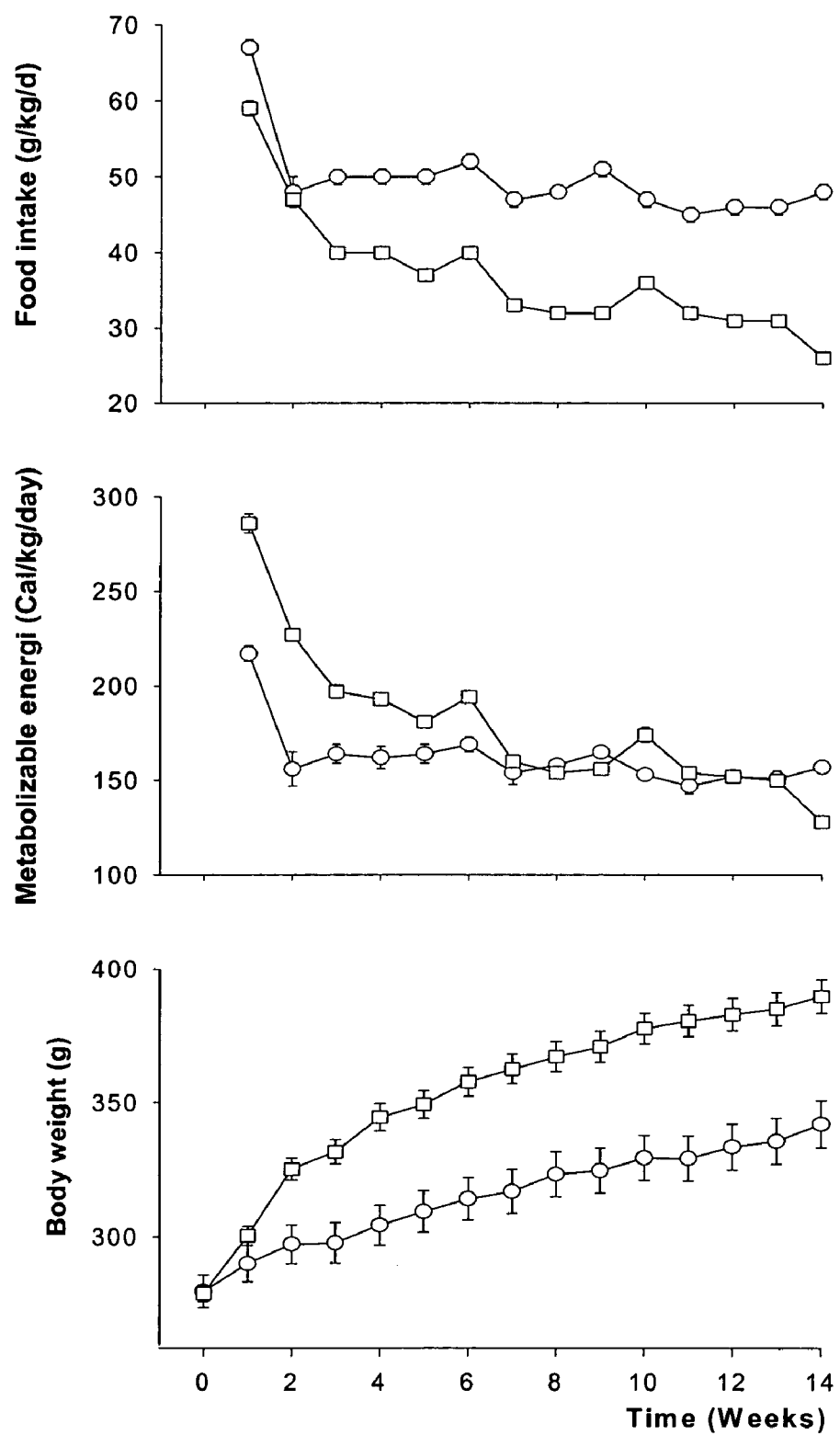

PREVENTION OF HYPERINSULINEMIA IN SUBJECTS UNDERGOING GROWTH HORMONE (GH) TREATMENT

CROSS-REFERENCE TO RELATED APPLICATIONS

This application is a continuation of U.S. patent application Ser. No. 10/822,020, filed Apr. 9, 2004 now abandoned, and claims priority under 35 U.S.C. § 119 of Danish Patent Application No. PA 2003 00548, filed Apr. 9, 2003, and U.S. Provisional Patent Application No. 60/467,07, filed May 1, 2003, the contents of which are fully incorporated herein by reference.

BACKGROUND OF THE INVENTION

Obesity is known to be associated with serious risk factors, and there is currently intense interest in identifying new principles for treatment of this condition. These efforts have hitherto resulted in identification of a substantial number of potential central and peripheral targets for treatment. It has also been shown that growth hormone (GH), more specifically human growth hormone (hGH) in human beings, acts as a potent regulator of body fat storage, and thus promotes breakdown of adipose tissue in obese humans while preserving lean tissues. Since a large proportion of glucose disposal and energy expenditure is thought to take place in lean tissues, preservation of such tissues combined with a selective loss of adiposity appears to be a highly desirable objective.

Although it is known that the protein anabolic aspect of the GH—insulin like growth factor-1 axis is influenced by diet composition, there does not appear to have been any focus on the question of whether this is also true for GH-stimulated loss of adipose tissue. The effect of GH during restriction of energy intake has also been unclear. There have been some reports indicating no additional effects of GH administration compared to the effect of energy restriction alone, whilst other reports have indicated the such effects.

A recently reported study by the present inventors and co-workers indicated GH-stimulated breakdown of adipose tissue in genetically intact old rats that had become obese while receiving a high-fat diet. However, despite normalisation of body fat stores following GH injection, basal insulin levels were significantly elevated.

It has been suggested that an excessive hyperinsulinemic response to GH injections would decrease the net effect of GH on adipose tissue. This would not be surprising since GH and insulin have been suggested to have opposing effects in adipose tissue. Moreover, sustained hyperinsulinemia would also increase the risk of development of overt Type 2 diabetes in susceptible obese individuals that already are at risk.

There is thus a clear need to identify factors determining the insulin response to administration of GH, both from a mechanistic and a safety point of view. The present inventors have now obtained clear indications that the macronutrient composition of the diet received by obese individuals constitutes one such factor, and that total energy intake constitutes another.

SUMMARY OF THE INVENTION

The present inventors have found that the insulin response in a subject to administration of GH can be modulated, for example, by varying diet composition and caloric intake, and/or by administering a drug which brings about a reduction in blood lipid levels (more precisely a reduction in the level of one or more blood lipid components), and that this influences adipose tissue loss and serum leptin levels. Among blood lipid components, free fatty acids (FFA) are of particular interest since high FFA levels often are associated with a decrease in insulin sensitivity leading to a compensatory hyper-secretion of insulin. A broad aspect of the invention thus relates to a method for substantially preventing hyperinsulinemia in an animal or human subject undergoing treatment with growth hormone (GH), the method comprising subjecting the subject, during the growth hormone treatment period, to one or more measures (such a diet regimen and/or a drug treatment) which cause a reduction in blood lipid levels (more precisely a reduction in the level of one or more blood lipid components). Further aspects of the invention include, inter alia:

(i) a method for achieving breakdown of adipose tissue in an animal or human subject substantially without induction of hyperinsulinemia in the subject, the method comprising administering a growth hormone (GH) to the subject whilst subjecting the subject to one or more measures which cause a reduction in blood lipid levels (more precisely a reduction in the level of one or more blood lipid components);

(ii) a method for reducing blood lipid levels (more precisely reducing the level of one or more blood lipid components) in an animal or human subject substantially without induction of hyperinsulinemia in the subject, the method comprising administering a growth hormone (GH) to the subject whilst inhibiting lipolysis in the subject; and (iii) a method for reducing blood lipid levels (more precisely reducing the level of one or more blood lipid components) in an animal or human subject substantially without induction of hyperinsulinemia in the subject, the method comprising administering a growth hormone (GH) to the subject whilst stimulating lipid clearance from circulation.

Other aspects of the invention include medical kits suitable for use in methods according to the invention.

Further detailed aspects of the invention are described below.

LIST OF FIGURES

FIG. 1. Intakes of food and metabolizable energy, and body weight development during the "fattening" period before GH dosing in old rats fed a high-fat (HF) diet (□—□, n=58) or a low-fat (LF) diet (○—○, n=23). Data represent means ±SE.

Figure 2:
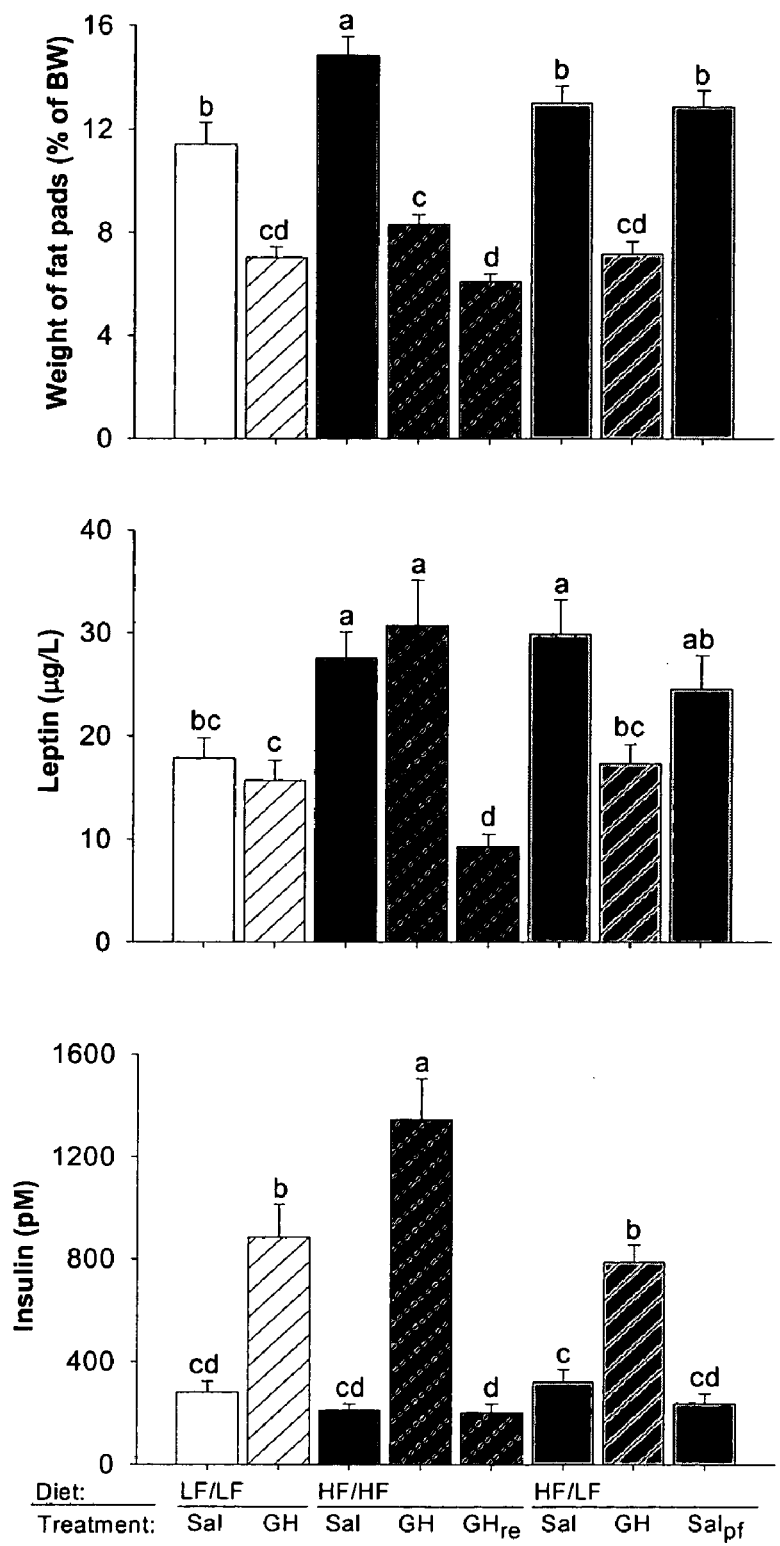

FIG. 2. Adipose tissue weight in relation to body weight and plasma concentrations of leptin and insulin, in old rats injected with growth hormone (GH) or saline (Sal). LF/LF signifies that animals were fed a low-fat (LF) diet both in the "fattening" period before GH dosing and during a 3-week GH-dosing period. By analogy, HF/HF signifies that a high-fat (HF) diet was provided in both periods, whereas HF/LF signifies that rats were shifted from the HF diet to the LF diet as GH dosing began. The suffixes/subscripts "re" and "pf" denote diet restriction and pair-feeding, respectively (for details, see Table 2). Data represent means ±SE (n=11–12).

Figure 3:
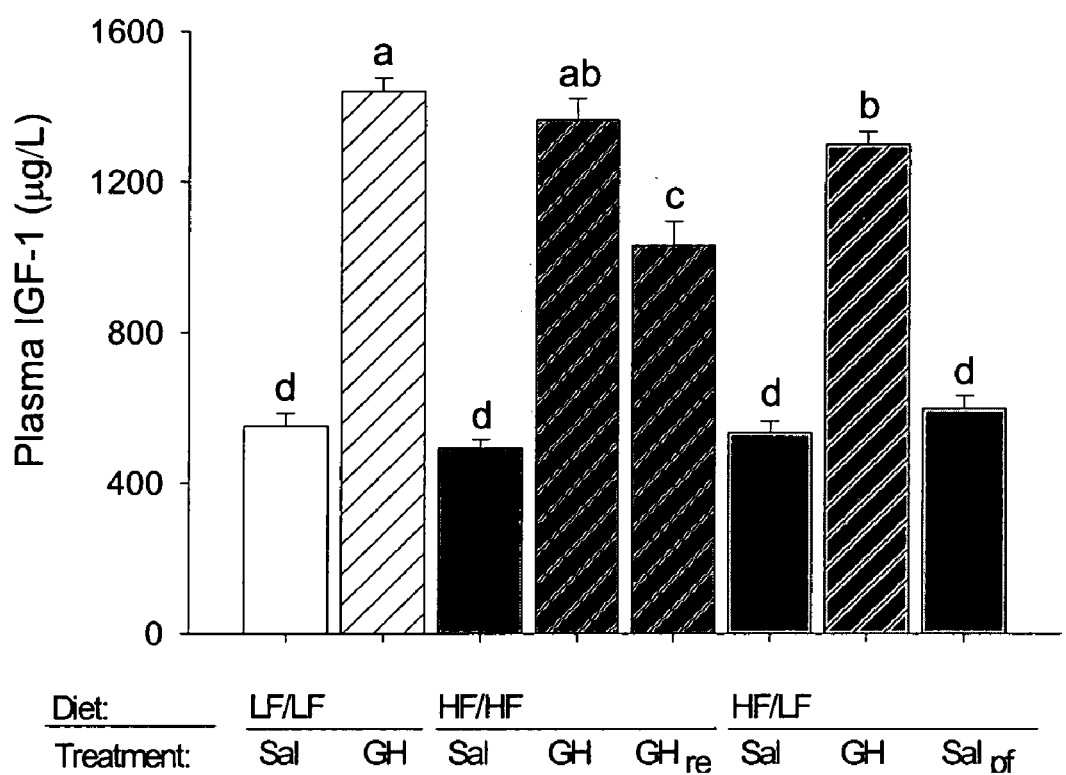

FIG. 3. Plasma insulin-like growth factor-1 (IGF-1) levels in old rats injected with growth hormone (GH) or with saline (Sal). LF/LF signifies that animals were fed a low-fat (LF) diet both in the "fattening" period before GH dosing and during a 3-week GH-dosing period. By analogy, HF/HF signifies that a high-fat (HF) diet was provided in both periods, whereas HF/LF signifies that rats were shifted from the HF diet to the LF diet as GH dosing began. The suffixes/subscripts "re" and "pf" denote diet restriction and pair-feeding, respectively (for details, see Table 2). Data represent means ±SE (n=11–12).

Figure 4:
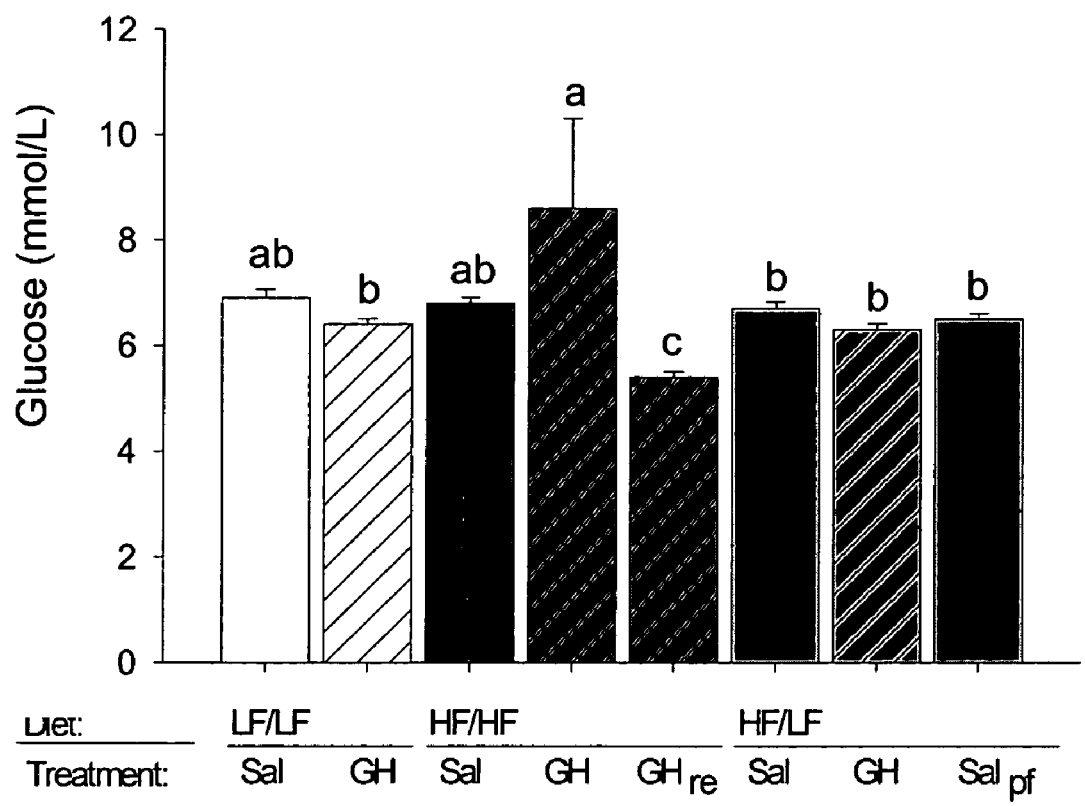

FIG. 4. Plasma concentrations of glucose in old rats injected with growth hormone (GH) or with saline (Sal). LF/LF signifies that animals were fed a low-fat (LF) diet both in the "fattening" period before GH dosing and during a 3-week GH-dosing period. By analogy, HF/HF signifies that a high-fat (HF) diet was provided in both periods, whereas HF/LF signifies that rats were shifted from the HF diet to the LF diet as GH dosing began. The suffixes/subscripts "re" and "pf" denote diet restriction and pair-feeding, respectively (for details, see Table 2). Data represent means ±SE (n=11–12).

DETAILED DESCRIPTION OF THE INVENTION

The present invention provides methods and compositions for minimizing the risk of development of diabetes as a consequence of excessive overloading of insulin-producing beta-cells.

One aspect of the present invention relates to a method for substantially preventing hyperinsulinemia in an animal or human subject undergoing treatment with growth hormone (GH), the method comprising subjecting the subject, during the growth hormone treatment period, to one or more measures which cause a reduction in blood lipid levels. The method in question is believed to be of general applicability, irrespective of the underlying rationale for treatment of the subject with growth hormone. Thus, for example, the method of the invention may be used in the context of established GH treatments of immature humans (children or adolescents), such as for the purpose of stimulating growth to counteract development of short stature or dwarfism, as well as of mature (adult) humans.

A closely related further aspect of the invention relates to a method for achieving breakdown of adipose tissue in an animal or human subject—particularly an obese human subject—substantially without induction of hyperinsulinemia in the subject, the method comprising administering a growth hormone (GH) to the subject whilst subjecting the subject to one or more measures which cause a reduction in blood lipid levels.

Measures of the type referred to in relation to methods of the invention include, without limitation, diet regimens or drug treatments. In one embodiment, the subject is provided with restricted amounts of a high-fat (HF) diet as sole food source (nutrition source). Appropriate drug treatments include, without limitation, treatment with agents such as the antihyperlipoproteinemic Acipimox™ (Olbetam™), i.e. 5-methylpyrazinecarboxylic acid 4-oxide, and related compounds (see U.S. Pat. No. 4,002,750); statins, such as Fluvastatin™, Lovastatin™, Pravastatin™ or Simvastatin™; and fibrates, such as Bezafibrat™, Clofibrat™ or Gemfibrozil™, in amounts and dosage regimens that are effective in lowering blood lipid levels.

Another, related aspect of the present invention relates to a method for reducing blood lipid levels in an animal or human subject substantially without induction of hyperinsulinemia in the subject, the method comprising administering a growth hormone (GH) to the subject whilst providing the subject with restricted amounts of a high-fat (HF) diet as sole food source.

A still further aspect of the invention provides another method for reducing blood lipid levels in an animal or human subject substantially without induction of hyperinsulinemia in the subject, the method comprising administering a growth hormone (GH) to the subject whilst inhibiting lipolysis in the subject. In this connection, inhibition of lipolysis may be reflected in inhibition of the lipase known as Hormone-Sensitive Lipase (HSL), although inhibition of other families of lipases may also be of relevance in the context of the method in question according to the invention. Non-limiting examples of substances capable of inhibiting the lipolytic effect of HSL include those disclosed in U.S. Pat. No. 6,596,742 B1 (corresponding to WO 01/17981), WO 01/66531, WO 03/051841, WO 03/051842 and WO 03/105860.

Yet another aspect of the invention relates to a method for reducing blood lipid levels in an animal or human subject substantially without induction of hyperinsulinemia in the subject, the method comprising administering a growth hormone (GH) to the subject whilst stimulating lipid clearance from the circulation. In this connection, stimulation of clearance of lipid from the circulation may, for example, be achieved by administration of a substance which acts to stimulate, activate or potentiate a lipase such as Lipoprotein Lipase (LPL). Non-limiting examples of LPL-potentiating substances include those described in WO 01/27088.

With regard to what constitutes "restricted" amounts of a HF diet in the context of the invention, it is generally preferable that the energy content (caloric content) of the amount of HF diet with which the subject is provided does not exceed (i.e. is below or is equal to or at least approximately equal to) the theoretical maintenance level for the subject in question. In the case of human subjects, there is an extensive body of published data which enables the establishment of the theoretical maintenance level for an individual on the basis of parameters such as age, gender, weight, height, ethnicity and level of physical activity. Published sources of such data include: Ritz, P., *Factors affecting energy and macronutrient requirements in elderly people*, Public Health Nutrition 4 (2001) pp. 561–569; and Lin et al., *Estimation of energy requirements in a controlled feeding trial*, Am. J. Clin. Nutr. 77 (2003) pp. 639–645.

With regard to animal species, particularly "farm" animals (animals of importance in relation to production of meat products, dairy products, eggs and the like, such as cattle, pigs, goats and poultry), and other domestic animals, such as horses, data are available from sources such as the UK Agricultural Research Council (ARC), the Commonwealth Agricultural Bureau, and the US National Research Council (NRC; e.g. data from 1988 and 1998, published by National Academy Press, Washington D.C.).

In some embodiments, the present invention relates to the treatment of humans, in particular obese humans. In these embodiments, the growth hormone to be employed will preferably be human growth hormone (hGH).

In the light of the above methods of the invention, still further aspects of the present invention include the following:

(i) Pharmaceutical compositions comprising, as active ingredients, a growth hormone and an agent selected from: agents capable of reducing blood lipid levels; lipolysis-inhibiting agents (e.g. HSL inhibitors); and lipase-activating or -potentiating agents (e.g. LPL activators or potentiators);

(ii) Medical kits suitable for use in methods according to the invention and comprising a growth hormone preparation and one or more measures which cause a reduction in blood lipid levels, such as, e.g., a medical kit comprising a growth hormone preparation and a high-fat diet, a medical kit comprising a growth hormone preparation and a drug which causes a reduction in blood lipid levels, a medical kit comprising a growth hormone preparation and a lipolysis-inhibiting agent (such as an HSL inhibitor), or a medical kit comprising a growth hormone preparation and a lipolysis-activating or -potentiating agent (such as a LPL activator or potentiator).

Also encompassed by the invention is the use of a substance which acts as a growth hormone secretagogue (GHS; also known, inter alia, as a growth hormone releasing substance), i.e. a substance which, when administered to a subject by an appropriate route, is capable of stimulating the release of growth hormone from the pituitary of the subject, as an alternative to a GH per se in the various aspects of the invention (i.e. as an active ingredient in methods, pharmaceutical compositions, medical kits etc. as described above). Non-limiting examples include the synthetic hexapeptide His-D-Trp-Ala-Trp-D-Phe-Lys-NH$_2$, also known as GHRP-6 (see, e.g., Bowers et al. in *Endocrinology* 114 (1984) pp. 1537–1545 and in *Endocrinology* 128 (1991) pp. 2027–2035) and the peptide derivatives described in WO 95/17423. Naturally occurring growth hormone releasing substances of potential relevance in the context in question include so-called "growth hormone releasing hormone" (often abbreviated GHRH or GHRH(1–44)NH$_2$) and truncated forms thereof (see, e.g., Guillemin et al., *Science* 218 (1982) pp. 585–587 and Rivier et al., *Nature* 300 (1982) pp. 276–278).

Pharmaceutical Administration

The regimen for treatment of a given subject/patient with growth hormone and, where appropriate, with another drug, in the manner described herein, may be determined by one skilled in the art. The daily dose to be administered can be determined by a physician and will depend on the particular substance employed, on the route of administration and on the age and the condition of the subject or patient. A convenient daily dosage of GH is typically in the range of from about 0.001mg/kg body weight to about 2.0 mg/kg body weight, often from about 0.01 mg/kg body weight to about 1.0 mg/kg body weight. The therapeutic dose of the substance will depend upon the frequency and mode of administration, the sex, age, weight and general condition of the subject treated, the nature and severity of the condition treated and any concomitant diseases to be treated and other factors evident to those skilled in the art.

GH may be administered in a single dose or in repeated doses during the day. Administration in the manner described herein should continue until the treated individual is no longer in need of such treatment, for example, until an initially obese individual is no longer obese.

The route of GH administration may be any route that effectively transports the active compound to the appropriate or desired site of action, such as by infusion (continuous or pulsatile), injection, pulmonary inhalation, or by oral or nasal administration. Presently preferred routes include parenteral routes (e.g. via intramuscular, intraperitoneal, intravenous or subcutaneous injection, or by implant). The growth hormone can be formulated in dosage forms appropriate for each route of administration. The compositions or dosage forms may be in conventional forms, e.g. aerosols, solutions or suspensions.

A GH composition may be in a form suited for systemic injection or infusion, and may, as such, be formulated with a suitable liquid vehicle such as sterile water or an isotonic saline or glucose solution. The compositions may be sterilized by conventional sterilization techniques which are well known in the art. The resulting aqueous solutions may be packaged for use as such, or they may be filtered under aseptic conditions and lyophilized, the lyophilized preparation being combined with the appropriate sterile aqueous vehicle prior to administration. The composition may contain pharmaceutically acceptable auxiliary substances as required to approximate physiological conditions, such as buffering agents, tonicity-adjusting agents and the like. Non-limiting examples of buffering agents include citrate salts and histidine; non-limiting examples of tonicity adjusting agents include sugars, such as sucrose and mannitol, and salts, such as alkali metal and alkaline earth metal chlorides, e.g. sodium, potassium or calcium chloride, and the like. Examples of liquid carriers are syrup, peanut oil, olive oil, phospholipids, fatty acids, fatty acid amines, polyoxyethylene and water. Aqueous liquid formulations, in particular, may advantageously contain a non-ionic surfactant, e.g. a polysorbate [such as polysorbate 20 (e.g. Tween™ 20) or a poloxamer [such as poloxamer 188 (e.g. Pluronic™ F68) or poloxamer 407 (e.g. Lutrol™ F127)], and a preservative, such as benzyl alcohol, phenol or a cresol (e.g. m-cresol), will often be incorporated.

It may be advantageous to provide GH in the form of a sustained release formulation. As such, the composition may be formulated as microcapsules or microparticles containing the growth hormone encapsulated in, or dispersed in, a suitable pharmaceutically acceptable biodegradable polymer, such as polylactic acid, polyglycolic acid or a lactic acid/glycolic acid copolymer.

For nasal administration, the GH preparation may contain growth hormone dissolved or suspended in a liquid carrier, in particular an aqueous carrier, for aerosol application. The carrier may contain additives such as solubilizing agents (e.g. propylene glycol), surfactants, absorption-enhancers such as lecithin (phosphatidylcholine) or cyclodextrin, or preservatives such as parabenes.

Growth hormone may be formulated by any of the established methods of formulating pharmaceutical compositions, e.g. as described in *Remington: The Science and Practice of Pharmacy* (1995).

A liquid hGH formulation which is well suited, in particular, for administration by injection in the context of the present invention is Norditropin™ SimpleXx™ (Novo Nordisk).

Definitions

High-fat (HF) diet: A high-fat diet for humans, includes, without limitation, that given by M. R. Freedman et al. in a review article in *Obesity Research* 9, Suppl. 1 (March 2001) pp. 1S–40S. With reference to humans, the following table provides appropriate definitions not only of high-fat (HF) diets in the context of the present invention, but also of moderate-fat (MF) and low-fat (LF) diets:

TABLE

| | Caloric composition of diets* | | |
|---|---|---|---|
| Diet type | Fat (% kcals) | Carbohydrate (% kcals) | Protein (% kcals) |
| High-fat (HF) | 55–65 | <20% | 25–30 |
| Moderate-fat (MF) | 20–30 | 55–60 | 15–20 |
| Low-fat (LF) | 11–19 | >65 | 10–20 |

*M. R. Freedman, J. King and E. Kennedy, Popular diets: a scientific review, Obesity Research 9, Suppl. 1 (March 2001) pp. 1S-40S Obesity: the terms "obesity" and "obese" when employed in the context of the present invention imply an excess of adipose tissue. In this context obesity is best viewed as any degree of excess adiposity that imparts a health risk. The distinction between normal and obese individuals can only be approximated, but the health risk imparted by obesity is probably a continuum with increasing adiposity. However, in the context of the present invention, human individuals with a body mass index (BMI=body weight in kilograms divided by the square of the height in meters) above 25 are to be regarded as obese.

Growth hormone (GH): Growth hormone is a hormone that stimulates growth of all tissues capable of growing. Growth hormone is released from the pituitary. The release is under tight control of a number of hormones and neurotransmitters, either directly or indirectly. Growth hormone release can be stimulated by growth hormone releasing hormone (GHRH; vide supra) and inhibited by somatostatin. In both cases, the hormones are released from the hypothalamus, but their action is mediated primarily via specific receptors located in the pituitary. In the present context "growth hormone" may be growth hormone of any origin, e.g. avian, bovine, equine, human, ovine, porcine, salmon, trout or tuna growth hormone. Human growth hormone (hGH) will normally be preferred for the treatment of humans. The growth hormone used in accordance with the invention may be native growth hormone isolated from a natural source, e.g. by extracting pituitary glands in a conventional manner, or a growth hormone produced by recombinant techniques, e.g. as described in E. B. Jensen and S. Carlsen in *Biotech and Bioeng.* 36 1990) pp. 1–11. The term growth hormone (GH) in the context of the invention also encompasses: truncated forms of GH, i.e. truncated forms of a growth hormone wherein one or more amino acid residues has/have been deleted; GH analogues, wherein one or more amino acid residues in the native molecule has/have been substituted with another amino acid residue, preferably a residue of a naturally occurring amino acid, as long as the substitution does not lead to any adverse effect such as antigenicity or reduced activity; and GH derivatives, e.g. deamidated or sulfoxidated forms of the growth hormone, or forms having an N- or C-terminal extension (such as Met-hGH, Met-Glu-Ala-Glu-hGH or Ala-Glu-hGH). Other GH derivatives of relevance include those in which a GH (or biologically active fragment thereof) is conjugated to a molecule such as an albumin, e.g. human serum albumin (see, e.g., WO 97/24445), or a water-soluble polymer such as a polyethyleneglycol (PEG) (see, e.g., WO 03/044056), in order to achieve, e.g., protracted duration of GH activity. As mentioned above, among growth hormones per se, the preferred growth hormone in relation to treatment of humans is normally hGH (i.e. natural human growth hormone, or recombinantly produced human growth hormone which is identical to the natural hormone). Methionylated human growth hormone may, however, often be employed.

Blood lipids: Lipids are generally defined as being a group of fats, fat-derived substances and fatlike substances that are of low solubility in water, are soluble in organic solvents such as benzene, chloroform and ether, and are utilizable by animal organisms. They are easily stored in the body, serve as a source of fuel (energy), are important constituents of cell structure, and serve other physiological functions. Lipids may be considered to include neutral fats, fatty acids, certain steroidal substances (e.g. sterols) and certain waxes.

Fats: Fats (neutral fats) are glyceryl esters of higher fatty acids (such as stearic and palmitic acid), and include, in particular, triglycerides (glyceryl esters in which each of the three hydroxy groups of glycerol is esterified with a fatty acid).

Fatty acids: Fatty acids are generally defined as being straight-chain, saturated and unsaturated monocarboxylic acids in which the carboxylic acid group is terminal, and which have a total (usually even-numbered) of from 4 to 22 (sometimes 24) carbon atoms.

Steroidal substances: These include, e.g., cholesterol (a sterol). In blood, cholesterol is transported primarily in the form of various lipoproteins, e.g. the so-called low-density lipoproteins (LDL) and high-density lipoproteins (HDL). In analyses of lipid levels, e.g. in blood, cholesterol is often determined as total cholesterol, i.e. the sum total level of all forms of cholesterol present in the blood.

In blood, lipids of major importance include triglycerides, fatty acids [i.e. free fatty acids (FFA)], and cholesterol.

Usage of the terms "lipid", "fat", "fatty acid", "triglyceride", "cholesterol" and "total cholesterol" in relation to blood lipids and levels thereof in the context of the present invention is in accordance with the definitions and explanation given above.

Hyperinsulinemia

As used herein, hyperinsulinemia encompasses a fasting plasma level of insulin greater than the normal range, which may be, e.g., about 30 µIU (micro international units) per ml. Insulin may be measured by any conventional method, including, e.g., radioimmunoassay (Pharmacia, Medical Research Laboratories International).

Prevention of hyperinsulinemia encompasses the clinical observation that a patient receiving GH therapeutically does not exhibit a significant rise in fasting plasma insulin levels over that exhibited by the same patient prior to GH treatment. It also encompasses the clinical observation that a patient receiving GH therapy, who exhibits hyperinsulinemia consequent to the GH treatment, exhibits a detectable reduction in fasting plasma insulin levels once the measures of the invention (e.g., restricted high-fat diet and/or lipid-lowering drugs) have been added to the treatment regimen.

The following are intended as non-limiting examples of the present invention.

EXAMPLE 1

Effects of Diet and GH on Body Composition, Blood Lipids, and Insulin

The following experiments were performed in order to evaluate the effect of varying diet on the effect of GH administration on insulin levels and other metabolic parameters.

Materials and Methods

Animals and Test Substances

Female Wistar rats weighing about 260 g were purchased 1 month before the start of experiments from Møllegård Breeding and Research Centre (Lille Skensved, Denmark). On arrival, rats were placed in conventional rat cages housing 2–3 animals. They were weighed weekly, and had free access to drinking water and a standard rat feed. All diets, including the experimental diets (see Table 1, below), were purchased from a local feed supplier (Brogaarden, Gentofte, Denmark). The experimental protocol was approved by the Danish national ethical committee for animal experiments (Dyreforsøgstilsynet, Copenhagen, Denmark). The growth hormone (GH) used in the present study was recombinantly produced human GH (hGH) from Novo Nordisk A/S (Bagsværd, Denmark).

Experimental Procedures

At an age of 12 months, rats were randomly assigned to receive either a high-fat (HF) diet [number of rats (n)=58] or a low-fat (LF) diet (n=23) (Table 1).

TABLE 1

Composition of high-fat (HF) and low-fat (LF) diets with theoretical energy content (percent) in parentheses.

|  | Diets HF | LF |
|---|---|---|
| Ingredients (g/kg) |  |  |
| Maize meal | 493 | 818 |
| Wheat bran | 27 | 27 |
| Casein | 148 | 110 |
| Animal fat | 300 | 13 |
| Vitamins and minerals | 32 | 32 |
| Chemical composition (g/kg) |  |  |
| Crude protein (energy %) | 170 (18%) | 170 (25%) |
| Crude fat (energy %) | 320 (55%) | 50 (12%) |
| Carbohydrates, total | 344 (27%) | 565 (63%) |
| Crude fibre | 17 | 26 |
| Disaccharides | 11 | 18 |
| Polysaccharides | 316 | 521 |
| Metabolizable energy (Mcal/kg) | 4.8 | 3.2 |
| Fatty acids |  |  |
| Total (% of crude fat) | 94 | 92 |
| Saturated (% of total) | 49 | 25 |
| Mono-unsaturated (% of total) | 39 | 30 |
| Poly-unsaturated (% of total) | 12 | 45 |

The diet in question was continued for 14 weeks, during which body weight development was recorded (FIG. 1). During this time, rats were assigned to 8 groups for dosing of GH thereafter, as indicated in Table 2.

TABLE 2

Allocation of rats to high-fat (HF) and low-fat (LF) diets during a 14-week period before dosing and during a 3-week period of dosing with either saline or growth hormone (GH). GH was administered in a total dose of 4 mg/kg/day, divided into two injections.

| Diet before dosing | Diet during dosing | Dosing | n | Denomination |
|---|---|---|---|---|
| Low Fat | Low Fat | Saline | 11 | LF/LF-Sal |
|  |  | GH | 12 | LF/LF-GH |
| High Fat | High Fat | Saline | 12 | HF/HF-Sal |
|  |  | GH | 11 | HF/HF-GH |
|  | Energy restricted* | GH | 12 | HF/HF-GHre |
|  | Low Fat | Saline | 11 | HF/LF-Sal |
|  |  | GH | 12 | HF/LF-GH |
|  | Pair fed* | Saline | 12 | HF/LF-Salpf |

*Age- and weight-matched rats were fed the same amount of metabolizable energy consumed by HF/LF-GH-group. In the HF/HF-GHre group, this was achieved by restricting food intake (energy-restricted), whereas rats in the HF/LF-Salpf group were pair-fed with the HF/LF-GH group. Both these groups were run behind the others.

Injection of GH continued for 3 weeks, after which the rats were sacrificed by decapitation. After bleeding, serum and plasma were prepared and frozen at −80° C.

The large fat pad embedding the kidneys (denoted perirenal fat), and fat pads around the uterus, ovaries and intestines (denoted body fat or adipose tissue ) were quickly dissected. After dissection the adipose tissue was weighed and frozen at −80° C. One thigh muscle, the quadriceps femoris, was also dissected and weighed.

With a view, inter alia, to supplementing measurements of changes in levels of blood lipids, glycerol and β-hydroxybutyrate (BHBT) as a consequence of the administration of GH or saline in combination with the various diet regimens, a series of similar experiments of shorter duration (4 days) was conducted using 45 rats (n=15 in each group) that were all obese due to 10 weeks of feeding with high-fat (HF) diet. All the animals in question received a low-fat (LF) diet during the 4-day treatment period. They were divided into three groups receiving (a) saline alone, (b) GH and (c) saline in combination with pair-feeding with the GH group.

Chemical Analyses

The content of fat in muscle tissue was analysed by Bioteknologisk Institut (Kolding, Denmark) using gas chromatography and employing standardized methods. Plasma concentrations of metabolites were determined with a Synchron™ CX5 auto-analyzer system (Beckman Instruments, Fullerton, USA).

Blood Analyses

Concentrations of lipids, glycerol and β-hydroxybutyrate (BHBT) were likewise determined using a Synchron™ CX5 auto-analyzer system (Beckman Instruments, Fullerton, USA).

Hormone Assays

Total plasma IGF-I was measured after acid-ethanol extraction as previously described (19); the intra-assay and inter-assay coefficients of variation were 6% and 13%, respectively. Plasma insulin was determined using an assay described previously (20); the intra- and inter-assay coefficients of variation for this assay were 5.4% and 8.4% respectively. Plasma leptin was determined using a commercial kit from Linco research, Inc. (St Charles, USA); the intra- and inter-assay coefficients of variation were 4.6% and 5.7%, respectively.

Statistical Analyses

All experimental data were entered into the 6.11 version of the SAS statistical software program, whereby descriptive statistics were calculated using the univariate procedure (SAS Inc, Cary, USA). Before further analysis, data were checked for normal distribution. In some cases where deviations were found, data were logarithmically transformed to achieve such a distribution. Potential differences between treatment groups were tested with a one-way analysis of variance (GLM procedure of SAS) followed by Duncan's multiple-range test. In most cases these tests were performed with an α-value of 0.05, but where applicable an α-value of 0.01 was used. Data are presented as means ±standard error (SE).

Results

Body Weight Gain and Feed Consumption in the Period Before GH Dosing

At the start of the 14-week "fattening" period, rats in the HF group and the LF group had body weights of 279±3 and 280±6 g, respectively. Rats in the HF group gained 111±5 g in body weight during the 14 week period. Rats receiving the LF diet gained 63±5 g, which was significantly ($p<0.01$) lower. This resulted in significant ($p<0.01$) differences in live weights, viz. 390±6.4 (HF diet group) vs. 343±8.6 g (LF diet group).

As can be seen from FIG. 1, rats given the HF diet had a comparatively high intake of food, and consequently a comparatively high metabolizable energy intake in the first phase of the "fattening" period. This was followed by a clear decline, so that in the last phase, intakes of metabolizable energy in the two groups were similar.

Food Consumption During GH Dosing

As was the case during the "fattening" period, rats fed the LF diet during GH dosing consumed significantly ($p<0.05$) more food than did rats fed the HF diet (see Table 3, below), but due to the lower energy content of the LF diet the intakes of metabolizable energy were not significantly different between the two groups.

There was a general decrease in food intake in the first phase after commencement of GH injections (data not shown), thus confirming our previous observations (18). Measured over the three-week dosing period, this effect remained statistically significant for rats fed the LF diet (Table 3). GH-treated rats which were switched from the HF diet to the LF diet successively increased their consumption between the second and third week of treatment, ending up with about the same total amount of food ingested as the corresponding saline-control rats. During this phase the pair-fed group could not follow the GH-treated group, and small food refusals were occasionally observed, resulting in a slightly lower total consumption of food (Table 3).

TABLE 3

Effects of growth hormone (GH) dosing on: consumption of high-fat (HF) and low-fat (LF) diets, body weights, adipose tissue, skeletal muscle weight and muscle content of fat. Food intake was registered per cage unit containing 2–3 animals (n = 6), and fat in muscle was analysed on a randomly selected number (n = 5) of animals from each group. In other cases, means ± SE are based on 11–12 observations.

| Diet before dosing | Diet during dosing | Dosing | Intakes | | | Body weight | | | Tissue weights and composition | | |
|---|---|---|---|---|---|---|---|---|---|---|---|
| | | | Food (g/kg/d) | Metabolizable energy (Cal/kg/d) | Protein (g/kg/d) | Start weight (g) | Final weight (g) | Change in weight (g) | Adipose tissue (g) | Skeletal Muscle (g) | Fat in Muscle (%) |
| Low-fat | Low-fat | Saline | $46^a \pm 2.0$ | $149^{ab} \pm 6.5$ | $7.8^a \pm 0.34$ | $345^{bc} \pm 13$ | $355^e \pm 11$ | $9.7^d \pm 3.6$ | $41^{bc} \pm 3.8$ | $2.3^b \pm 0.10$ | $4.4^a \pm 1.6$ |
| Low-fat | Low-fat | GH | $40^b \pm 1.9$ | $129^{bc} \pm 6.1$ | $6.8^b \pm 0.32$ | $341^c \pm 12$ | $419^{abc} \pm 11$ | $78^a \pm 3.7$ | $30^{de} \pm 2.3$ | $3.0^a \pm 0.07$ | $1.7^c \pm 0.2$ |
| High-fat | High-fat | Saline | $33^{cd} \pm 1.7$ | $158^a \pm 8.0$ | $5.6^{cd} \pm 0.28$ | $391^{ab} \pm 17$ | $400^{bcd} \pm 16$ | $9.0^d \pm 3.7$ | $60^a \pm 4.7$ | $2.3^b \pm 0.08$ | $3.1^{abc} \pm 0.9$ |
| High-fat | High-fat | GH | $29^d \pm 1.5$ | $142^{ab} \pm 7.2$ | $5.0^d \pm 0.25$ | $390^{ab} \pm 15$ | $452^a \pm 13$ | $62^b \pm 4.9$ | $38^{cd} \pm 2.7$ | $2.8^a \pm 0.11$ | $1.9^{bc} \pm 0.4$ |
| High-fat | Energy restricted* | GH | $22^* \pm 0.0$ | $106^* \pm 0.12$ | $3.7^* \pm 0.00$ | $389^{ab} \pm 9$ | $429^{ab} \pm 9$ | $40^c \pm 7.6$ | $26^e \pm 1.6$ | $3.0^a \pm 0.16$ | $1.8^{bc} \pm 0.1$ |
| High-fat | Low-fat | Saline | $37^{bc} \pm 2.4$ | $119^{cd} \pm 7.9$ | $6.2^{bc} \pm 0.42$ | $388^{ab} \pm 17$ | $381^{cde} \pm 16$ | $-7^e \pm 3.6$ | $50^{ab} \pm 4.5$ | $2.2^b \pm 0.09$ | $3.8^{ab} \pm 0.6$ |
| High-fat | Low-fat | GH | $33^{cd} \pm 2.8$ | $106^d \pm 9.0$ | $5.6^{cd} \pm 0.47$ | $389^{ab} \pm 16$ | $431^{ab} \pm 10$ | $41^c \pm 8.2$ | $31^{cde} \pm 2.7$ | $2.9^a \pm 0.07$ | $1.6^c \pm 0.3$ |
| High-fat | Pair fed* | Saline | $30^* \pm 2.1$ | $97^* \pm 6.7$ | $5.1^* \pm 0.35$ | $393^a \pm 17$ | $371^{de} \pm 15$ | $-22^e \pm 5.4$ | $49^b \pm 3.8$ | $2.2^b \pm 0.05$ | $2.8^{abc} \pm 0.4$ |

*Groups that did not have free access to food were excluded from statistical analyses of food intake variables.
a,b,c,d,e Differences between groups were tested with a one-way analysis of variance followed by Duncan's multiple range-test. Values within columns not sharing a common letter superscript differ significantly ($p < 0.05$).

TABLE 4

Effect of GH and diet on levels of blood lipids and related substances.

| Duration of Experiment | Diet before dosing | Diet during dosing | Dosing | FFA | Glycerol | BHBT | Triglyceride | Cholesterol |
|---|---|---|---|---|---|---|---|---|
| 4 Days | High-fat | Low-fat | Saline | $0.56 \pm 0.05$ | $0.33 \pm 0.01$ | $0.60 \pm 0.07$ | $0.69 \pm 0.09$ | $1.17 \pm 0.09$ |
| 4 Days | High-fat | Low-fat | GH | $0.63 \pm 0.07$ | $0.34 \pm 0.01$ | $1.32 \pm 0.24^4$ | $0.48 \pm 0.03^5$ | $0.64 \pm 0.05^7$ |
| 4 Days | High-fat | Pair-fed | Saline | $0.68 \pm 0.07$ | $0.30 \pm 0.01$ | $1.17 \pm 0.11^4$ | $0.39 \pm 0.03$ | $1.03 \pm 0.08$ |
| 21 Days | Low-fat | Low-fat | Saline | $0.75 \pm 0.08$ | $0.39 \pm 0.03$ | $0.25 \pm 0.04$ | $1.41 \pm 0.21$ | $1.39 \pm 0.10$ |
| 21 Days | Low-fat | Low-fat | GH | $0.43 \pm 0.04^1$ | $0.33 \pm 0.02^3$ | $0.24 \pm 0.02$ | $1.40 \pm 0.14$ | $1.01 \pm 0.08^7$ |
| 21 Days | High-fat | High-fat | Saline | $0.49 \pm 0.03$ | $0.35 \pm 0.03$ | $0.51 \pm 0.04$ | $0.88 \pm 0.09$ | $1.27 \pm 0.06$ |
| 21 Days | High-fat | High-fat | GH | $0.36 \pm 0.04^1$ | $0.39 \pm 0.02$ | $0.30 \pm 0.04$ | $1.54 \pm 0.12^6$ | $0.90 \pm 0.07^7$ |
| 21 Days | High-fat | Energy-restricted | GH | $0.20 \pm 0.01^2$ | $0.20 \pm 0.01^2$ | $0.92 \pm 0.09^2$ | $0.53 \pm 0.04^2$ | $0.82 \pm 0.03$ |
| 21 Days | High-fat | Low-fat | Saline | $0.60 \pm 0.06$ | $0.38 \pm 0.03$ | $0.17 \pm 0.03$ | $1.58 \pm 0.25$ | $1.21 \pm 0.10$ |
| 21 Days | High-fat | Low-fat | GH | $0.38 \pm 0.04^1$ | $0.30 \pm 0.01^3$ | $0.22 \pm 0.03$ | $1.27 \pm 0.13$ | $0.92 \pm 0.05^7$ |
| 21 Days | High-fat | Pair-fed | Saline | $0.74 \pm 0.07$ | $0.41 \pm 0.03$ | $0.50 \pm 0.07^4$ | $1.00 \pm 0.13$ | $1.28 \pm 0.06$ |

FFA = free fatty acids;
BHBT = β-hydroxybutyrate;
Cholesterol = total cholesterol.
All values in mM.
Superscript numbers indicate significant effects as follows: [1]GH lowered FFA level after 21 days compared to saline; [2]FFA, glycerol and triglyceride levels in the high-fat/energy restricted group were lower, while BHBT level was elevated, compared to the other GH-treated groups initially fed high-fat diet; [3]GH lowered glycerol levels in animals on low-fat diet compared to saline; [4]BHBT level elevated compared to saline;
[5]Triglyceride decreased after 4 days of GH treatment compared to saline, but not with the pair-fed group; [6]After 21 days, the combination of GH and high-fat diet caused elevated triglyceride levels compared to saline; [7]GH decreased the cholesterol level after both 4 and 21 days compared to saline lower, while BHBT level was elevated, compared to the other GH-treated groups initially fed high-fat diet; [3]GH lowered glycerol levels in animals on low-fat diet compared to saline; [4]BHBT level elevated compared to saline; [5]Triglyceride decreased after 4 days of GH treatment compared to saline, but not with the pair-fed group; [6]After 21 days, the combination of GH and high-fat diet caused elevated triglyceride levels compared to saline; [7]GH decreased the cholesterol level after both 4 and 21 days compared to saline Body Weight During Dosing Irrespective of diet, three weeks of GH treatment generally increased body weight (Table 3). A change of diet from HF to LF, combined with saline alone, produced a significant ($p<0.05$) reduction of live weight. Rats with the same dietary record which were pair fed with GH-treated counterparts also lost weight (Table 3).

Effects of Diet and GH on Body Composition

GH treatment significantly ($p<0.05$) decreased the weight of adipose tissue excised from rats fed HF or LF diet, or rats that were switched from HF to LF, both in absolute numbers (Table 3) and in relation to their body weight (FIG. 2). Pair-feeding alone did not significantly affect the weight of adipose tissue. In parallel with the reductions of adipose tissue weight seen in animals injected with GH, fresh muscle (Quadriceps femoris) weights generally increased significantly ($p<0.05$) (Table 3). When expressed in relation to body weight, this effect was not statistically significant in rats that were on the HF diet throughout the entire study. The fat content of muscle tissue was generally decreased in all groups injected with GH, although the decrease was not statistically significant in all instances (Table 3).

Effects of Diet and GH on Blood Lipids

The blood concentrations (levels) of free fatty acids (FFA), glycerol, β-hydroxybutyrate (BHBT), triglyceride and cholesterol (total cholesterol) are shown in Table 4. Serum FFA levels and total cholesterol levels were lowered significantly after 21 days of GH treatment, as was plasma glycerol, except during HF diet feeding. Triglyceride levels were elevated at that time, but only when GH was combined with HF diet. In contrast, triglycerides were markedly lowered by feeding restricted amounts of HF diet in combination with GH treatment, whilst no changes were seen in the other groups. Cholesterol levels were already low after 4 days of GH injection. BHBT increased initially following GH injection and pair-feeding. Only the group which received GH and restricted access to HF diet, and the pair-fed group, exhibited elevated BHBT levels after 21 days.

Effects of GH on Plasma Variables

Injection with GH produced a significant ($p<0.05$) increase of plasma IGF-1 concentrations irrespective of dietary regimen (FIG. 3). However, the increase was significantly ($p<0.05$) lower in animals with restricted access to the HF diet. Exceptionally low insulin and leptin levels were also observed in this group (FIG. 2), and glucose levels in this group were concomitantly significantly decreased in comparison to any other group (FIG. 4). In contrast, GH administration to animals with free access to the HF diet produced a marked hyperinsulinemia, and no fall in leptin levels was seen; glucose levels in these animals were likewise not significantly changed compared with levels in saline-control animals.

Discussion of Results

At the conclusion of the experiments described above, rats that had received the HF diet throughout contained about 30% more adipose tissue than rats fed the LF diet. This difference is likely founded in the phase when rats first were introduced to a HF diet, since in that phase their daily intake of metabolizable energy was clearly elevated for several weeks. After about 6 weeks, their caloric intake had fallen to the same level as that of rats fed the LF diet, indicating that although this adaptation is not as fast as has been observed in young animals, the old rats employed in the present work still retain some ability to regulate their caloric intake.

Injections of GH produced an increase in skeletal muscle weight, loss of adipose tissue and a transient decrease in food intake in those groups of animals that had free access to food. These effects were observed irrespective of whether rats were maintained on their habitual diets or were shifted from the HF to the LF diet. Shift of diet without GH injection, but with essentially the same caloric intake (pair-fed), produced a fall in body weight, but only marginal effects on adipose tissue weight. In view of this, it can be concluded that treatment with GH produces a significant and specific loss of adipose tissue. It also appears that promotion of fat loss is a consistent effect of GH under a variety of dietary conditions, but that modulation of this effect by the amount of diet eaten occurs. Thus, if the HF diet is fed in restricted amounts, the fat loss after GH injections is greater than if there is free access to the same diet (and thereby is greater consumption of metabolizable energy). This observation shows that caloric intake either directly or indirectly modulates the effect of GH on fat loss.

Surprisingly low plasma insulin levels were found in blood from animals which had been fed restricted amounts of the HF diet during GH treatment, whereas hyperinsulinemia was especially marked in the case of animals which had had free access to the same diet. The degree of adipose tissue breakdown was significantly different between these groups. The present inventors thus believe that they have identified a dietary situation whereby the hyperinsulinemic response to GH administration may be avoided, thus presenting the possibility of increasing both the efficacy and safety aspects of GH treatment of obese humans. It can be seen from Table 4 that this dietary situation is associated with significant reductions in blood lipid levels, especially in the case of FFA levels. This can most probably explain the low insulin levels since it is widely established that high FFA levels are associated with a decrease in insulin sensitivity, leading to a compensatory hyper-secretion of insulin. There is little doubt that prolonged and uncontrolled hyperinsulinemia represents a real hazard to the patient and must be taken seriously. For this reason the present invention is believed to be of considerable importance.

To summarize, the results reported herein demonstrate not only that GH mediates breakdown of adipose tissue under a variety of dietary conditions, but—very importantly and surprisingly—that induction of hyperinsulinemia can be prevented if GH treatment is combined with restricted feeding of a diet which is relatively low in carbohydrates and rich in fat, and that same treatment regimen also promotes a fall in plasma leptin levels.

The invention claimed is:

1. A method for reducing the incidence of a statistically significant rise in plasma insulin levels in an animal or human subject undergoing treatment with growth hormone (GH), comprising providing the subject, during the growth hormone treatment period, with a restricted amount of a high-fat (HF) diet as the sole food source.

2. The method of claim 1, wherein the energy content of the diet does not exceed the theoretical maintenance level for the subject.

3. The method of claim 2, wherein the subject is a human.

4. The method of claim 3, wherein the human is obese.

5. The method of claim 1, wherein the subject is a human.

6. The method of claim 5, wherein the human is obese.

* * * * *